United States Patent [19]
Sorensen et al.

[11] Patent Number: 5,919,698
[45] Date of Patent: Jul. 6, 1999

[54] DISINFECTION AND CLEANER OF CONTACT LENSES

[75] Inventors: Thomas Lykke Sorensen, Raleigh, N.C.; Flemming Mark Christensen, Neuilly-sur-Seine, France

[73] Assignee: Novo Nordisk A/S, Bagsværd, Denmark

[21] Appl. No.: 09/022,135

[22] Filed: Feb. 11, 1998

Related U.S. Application Data

[63] Continuation of application No. PCT/DK96/00404, Sep. 24, 1996.

[30] Foreign Application Priority Data

Sep. 25, 1995 [DK] Denmark ................................. 1070/95
Oct. 16, 1995 [DK] Denmark ................................. 1168/95

[51] Int. Cl.$^6$ ...................................................... C12S 9/00
[52] U.S. Cl. ........................... 435/264; 510/114; 422/28; 134/901
[58] Field of Search ..................................... 435/184, 188, 435/264, 222; 134/27, 901; 422/28, 30; 510/112, 114; 514/839, 840; 424/94.2, 94.64

[56] References Cited

U.S. PATENT DOCUMENTS

| | | |
|---|---|---|
| 4,670,178 | 6/1987 | Huth et al. . |
| 4,767,559 | 8/1988 | Kruse et al. ............................ 252/106 |
| 5,145,644 | 9/1992 | Park et al. ................................ 422/28 |
| 5,630,884 | 5/1997 | Huth .......................................... 134/27 |

FOREIGN PATENT DOCUMENTS

| | | |
|---|---|---|
| 1 146 881 | 5/1983 | Canada . |
| 0 147 100 | 7/1985 | European Pat. Off. . |
| 0 367 723 | 5/1990 | European Pat. Off. . |
| WO 86/07264 | 12/1986 | WIPO . |
| 89/11878 | 12/1989 | WIPO .................................... 134/901 |
| WO 93/17721 | 9/1993 | WIPO . |
| 94/16743 | 8/1994 | WIPO . |
| WO 95/02044 | 1/1995 | WIPO . |
| WO 95/16017 | 6/1995 | WIPO . |

*Primary Examiner*—William H. Beisner
*Attorney, Agent, or Firm*—Steve T. Zelson, Esq.; Reza Green, Esq.

[57] ABSTRACT

The present invention relates to a one-step method for disinfection and cleaning of contact lenses of the type using hydrogen peroxide as the disinfecting agent and a protease as the cleaning agent, comprising the following steps: a) disinfection of the contact lenses in an aqueous disinfecting solution comprising from 1 wt. % to 5 wt. % hydrogen peroxide at a pH not acceptable to the eyes, b) cleaning the contact lenses by subjecting the contact lenses to a protease being inactivated within a period of time at a pH level not acceptable to the eyes, c) neutralization of the hydrogen peroxide in the aqueous disinfecting solution with a microbial catalase being substantially active at pH 3.0 to 7.0, d) adjusting the pH in the aqueous disinfecting solution to a pH level acceptable to the eyes. Further, the invention relates to a tablet or capsule suitable for one-step disinfection and cleaning, a one-step disinfecting and cleaning system and further a one-step procedure for disinfection and cleaning contact lenses.

28 Claims, No Drawings

DISINFECTION AND CLEANER OF CONTACT LENSES

CROSS-REFERENCE TO RELATED APPLICATIONS

This application is a continuation of PCT/DK96/00404 filed on Sep. 24, 1996 and claims priority under 35 U.S.C. 119 of Danish application Ser. Nos. 1070/95 and 1168/95 filed on Sep. 25, 1995 and Oct. 16, 1995, respectively, the contents of which are fully incorporated herein by reference.

FIELD OF THE INVENTION

The present invention relates to a one-step method for disinfecting and cleaning contact lenses of the type using hydrogen peroxide as the disinfecting agent, a protease as the cleaning agent and a catalase for neutralizing the hydrogen peroxide in the aqueous disinfecting solution.

Further, the invention relates to a tablet or capsule suitable for one-step disinfection and cleaning, a one-step disinfection and cleaning system and further a one-step procedure for disinfection and cleaning contact lenses.

BACKGROUND OF THE INVENTION

Quite a lot of people today prefer wearing contact lenses to glasses. Some people use contact lenses for aesthetic reasons, as they believe that glasses make them look awkward. Other people value the freedom of movement that contact lenses give, which is advantageous when e.g. playing a game of soccer or attending a high-impact aerobics class. Then again some people just do not like the inconvenience of polishing greasy glasses.

Even though contact lenses have been improved during the last decades and posses many advantages in comparison to glasses, contact lenses still need to be disinfected and cleaned periodically, in most cases every day, to avoid infections and discomfort for the wearer.

The development of products for disinfection and cleaning of contact lenses have made the "daily task" easier. However, most contact lens users still regard the disinfection and cleaning task as a troublesome task.

Whether the contact lenses are hard or soft, opticians usually recommend to disinfect the lenses daily and clean them weekly.

Disinfection prevent growth of bacteria on the surface of the contact lenses which might lead to infection of the eyes and making it impossible to wear contact lenses for days.

Cleaning is normally performed by an enzyme capable of degrading debris and/or soil build up on the contact lenses surface. These deposits reduce the wearing comfort as only a reduced amount of oxygen is capable of penetrating the contact lenses to the eyes, and as the friction between the eyes and the contact lenses is increased.

After a cleaning and/or disinfection procedure the contact lenses need to be rinsed thoroughly to remove all enzymatic activity and/or disinfecting agent, e.g. by using a physiological saline solution.

In the case of the disinfecting agent being hydrogen peroxide a number of catalases have been known to be used as neutralizing agents.

Catalases E.C. 1.11.1.6 (Enzyme Nomenclature, Academic Press, Inc, 1992) are enzymes which catalyze the conversion of hydrogen peroxide ($H_2O_2$) to water ($H_2O$) and oxygen ($O_2$).

A plethora of methods for disinfection and cleaning of contact lenses are known. Proteases are often used for cleaning contact lenses as described in U.S. Pat. No. 3,910,296 (Allergan).

CA 1,146,881 (Bedding) concerns a method for cleaning contact lenses using enzymes, where the cleaning procedure is followed by rinsing of the lenses, e.g. with saline, to remove active enzymes from the lens.

U.S. Pat. No. 4,670,178 (Allergan) discloses a method for simultaneous cleaning and disinfection of contact lenses with a protease in hydrogen peroxide. The cleaning is effected by presence of protease activity and shown to be very efficient. After the cleaning and disinfection procedure the activity of the disinfecting and cleaning agent need to be removed from the lenses before use.

EP patent application No. 147,100 (Ciba Geigy) concerns cleaning and disinfection of contact lenses with a hydrogen peroxide solution in the presence of a solid sustained release composition which slowly releases a peroxide inactivator. The lenses may be treated with a wetting or comfort solution before inserting into the eyes. However, cleaning and disinfection with hydrogen peroxide does not remove proteinaceous deposits effectively from the surface of the contact lenses.

WO 86/07264 (Kellway Pharm. Ltd.) describes a method for disinfection and cleaning of contact lenses with hydrogen peroxide using a catalase immobilized in a container for neutralization of the hydrogen peroxide. This way excess hydrogen peroxide is decomposed without washing and rinsing.

WO 93/17721 (Genencor Int. Inc.) describes an improved method for cleaning and disinfection of contact lenses comprising disinfection with hydrogen peroxide and decomposition of the residual hydrogen peroxide in the solution with catalase enzyme (CatR) derived from the filamentous fungus *Aspergillus niger*.

WO 95/02044 (Novo Nordisk A/S) concerns two acidic proteases active in the presence of hydrogen peroxide in concentrations up to as high as 5 wt. %. Example 5 of said application describes cleaning and disinfection of contact lenses using one of said acidic proteases as the cleaning agent and hydrogen peroxide as the disinfecting agent. Further, it is mentioned that catalase may be used for neutralization of the hydrogen peroxide.

Cleaning and disinfection of contact lenses is regarded as a troublesome daily task by most contact lens wearer. Further, prior art methods for disinfection and cleaning of contact lenses are not very safe and consumer convenient as the risk of e.g. forgetting a step is very much present, as at least two not continuous steps need to be carried out.

Therefore, there is a need for more safe and consumer convenient disinfection and cleaning methods and systems. A one-step disinfecting and cleaning systems for contact lenses would increase the safety and consumer convenience.

SUMMARY OF THE INVENTION

The object of the present invention is to facilitate the daily troublesome task of disinfecting and cleaning contact lenses and to make the task more safe to perform.

In the first aspect the invention relates to a one-step method for disinfection and cleaning of contact lenses comprising the steps:

(a) disinfection of the contact lenses in an aqueous disinfecting solution comprising from 1 wt. % to 5 wt. % hydrogen peroxide at a pH not acceptable to the eyes, (b) cleaning the contact lenses by subjecting the contact lenses to a protease being inactivated within a period of time at a pH level not acceptable to the eyes, (c) neutralization of the hydrogen peroxide in the aqueous disinfecting solution with a microbial catalase being substantially active at pH 3.0 to 7.0, and (d) adjusting the pH in the aqueous disinfecting solution to a pH level acceptable to the eyes.

The invention also relates to a tablet or capsule for disinfection and cleaning of contact lenses, wherein the tablet is a multi-layer tablet, comprising:

(i) a protease being irreversibly inactivated within a period of time in an aqueous disinfecting solution at a pH level not acceptable to the eyes, and (ii) a microbial catalase being substantially active at pH 3.0 to 7.0, and (iii) an agent capable of adjusting the disinfecting solution to a pH acceptable to the eyes.

The invention is also directed toward a one-step system for disinfection and cleaning of contact lenses comprising:

(a) an aqueous disinfecting solution comprising 1 wt. % to 5 wt. % hydrogen peroxide, and (b) a tablet or capsule comprising
(i) a protease being irreversibly inactivated within a period of time in the aqueous disinfecting solution at a pH level not acceptable to the eyes, and
(ii) a microbial catalase being substantially active at pH 3.0 to 7.0,
(iii) an agent capable of adjusting the aqueous disinfecting solution to a pH acceptable to the eyes.

Finally the invention relates to a one-step procedure for disinfection and cleaning of contact lenses, comprising the steps of (1) soaking the contact lenses in a fixed amount of an aqueous disinfecting solution comprising 1 wt. % to 5 wt. % hydrogen peroxide, and (2) adding a tablet of the invention, and (3) storing the contact lenses in the aqueous disinfecting solution for a period of time.

DETAILED DESCRIPTION OF THE INVENTION

The object of the present invention is to facilitate the daily troublesome task of disinfecting and cleaning contact lenses and to make the task more safe to perform.

In the context of the present invention disinfection and cleaning of contact lenses is of the type involving the steps:

(a) disinfection of the contact lenses in an aqueous solution comprising between 1 wt. % and 5 wt. % hydrogen peroxide, especially 3 wt. % hydrogen peroxide, and (b) cleaning the contact lenses with a protease to remove debris and/or soil, and (c) neutralization of the hydrogen peroxide in the aqueous disinfecting solution with a catalase.

The present inventors have solved some of the problems of prior art disinfecting and cleaning systems by providing a more safe consumer convenient system.

A more safe and consumer convenient disinfecting and cleaning system means that the system, in comparison to corresponding prior art systems using the same above mentioned principles, have at least one of the following the following advantages:

reduces or eliminates the risk of using the system incorrectly (i.e. the system is more safe to use);

facilitates the disinfection and cleaning task for the contact lens user (i.e. more easy to use);

reduces the amount of steps to be performed by the contact lens user (i.e. less work to be done and less time are needed to perform the disinfection and cleaning task).

The present invention can be used for disinfection and cleaning of all types of contact lenses including hard, soft, rigid gas permeable lenses and silicone lenses etc.

The basic principle of the present invention is to use a suitable protease which is inactivated in the aqueous disinfecting solution during cleaning, due to e.g. pH influence, temperature influence or the like. Before being completely inactivated the protease must have had sufficient time and sufficient enzyme activity to clean the contact lenses.

It is to be understood that it is within the scope of the invention to use the disinfection and cleaning principle of the invention for corresponding disinfecting and cleaning procedures including separate disinfecting and cleaning (i.e. two-step methods).

In the first aspect the invention relates to a one-step method for disinfection and cleaning of contact lenses comprising the steps:

(a) disinfection of the contact lenses in an aqueous disinfecting solution comprising from 1 wt. % to 5 wt. % hydrogen peroxide at a pH not acceptable to the eyes, (b) cleaning the contact lenses by subjecting the contact lenses to a protease being inactivated within a period of time at a pH level not acceptable to the eyes, (c) neutralization of the hydrogen peroxide in the aqueous disinfecting solution with a microbial catalase being substantially active at pH 3.0 to 7.0, (d) adjusting the pH in the aqueous disinfecting solution to a pH level acceptable to the eyes.

A pH level not acceptable to the eyes means in the context of the present invention a pH within the ranges from about pH 8.0 to 13.0 and within the range about pH 1.0 to 6.0. A pH level acceptable to the eyes means a pH within the range from between about pH 6.0 to 8.0.

The above method of the invention may be performed in any of the following step sequences:

(i) a)-b)-c)-d), or (ii) a)-c)-b)-d), or (iii) a)-b)-d)-c), or (iv) a)-b)/c)-d), wherein step b) and step c) are performed simultaneously.

In a preferred embodiment of the method of the invention the aqueous disinfecting solution is a conventional commercial disinfecting solution comprising about 3 wt. % hydrogen peroxide at pH 3.5 (e.g. Oxysept®1 from Allegan).

At least in the context of the present invention "one-step" disinfection and cleaning means that the contact lens user's task consists of one continuous step only, which can be performed within few seconds and without any additional steps before the contact lenses are ready to wear.

The combined daily disinfection and cleaning makes the recommended weekly cleaning superfluous, as the amount of build-up debris and/or soil on the contact lenses' surfaces are diminished considerably. The daily disinfection and cleaning results in improved wearing comfort.

According to the invention all the present protease activity must be irreversibly inactivated within a fixed period of time to be defined.

If, for instance, the protease in question is to be irreversibly inactivated within a very short period of time the amount of protease must be relatively large to ensure cleaning of the contact lenses before complete inactivation of the protease. If, in contrast hereto, the protease in question is to be inactivated very slowly over a longer period of time only a very little amount of protease is needed.

The inactivation period for the protease may be from about 1 to 10 minutes to about 1, 2, 3 and no more than 4 hours.

A reduced amount of protease is needed when cleaning daily in comparison to cleaning weekly. The optimal amount of active protease to be added to the aqueous disinfecting solution to effectively clean the contact lenses before all protease activity has been inactivated by pH inactivation can easily be determined by a person skilled in the art.

Contemplated amounts of protease lies in the range from 0.5 $\mu$g to 50 $\mu$g preferably 1 $\mu$g to 25 $\mu$g, especially 2 $\mu$g to 10 $\mu$g enzyme protein/ml.

The protease used according to the invention may be any neutral, acidic or alkaline protease being irreversibly inactivated within a period of time (see above) in a disinfecting solution at a pH not acceptable to the eyes.

For instance, if the protease is an alkaline (or neutral) protease the pH of the aqueous disinfecting solution should be acidic in order to irreversible inactivate the protease.

Suitable proteases can be selected from the group comprising serine proteases, aspartic proteases, cysteine proteases and metallo proteases.

Also contemplated as suitable is truncated, modified or variants proteases of the above listed groups.

Examples of preferred serine proteases are trypsins, chymotrypsins and alkalophilic subtilisins.

Most preferred are the Bacillus derived alkaline serine proteases, such as subtilisin A, subtilisin BPN', subtilisin Carlsberg, subtilisin PB92, subtilisin 309, subtilisin 147, subtilisin 168, subtilisin DY, aqualysin or thermitase, truncations, modification and variants thereof.

Examples of cysteine proteases include papain and bromelain.

To the group of suitable metallo proteases are e.g. Neutrase® and collagenase.

Examples of aspartic proteases are e.g. pepsin A, pepsin B, pepsin C, chymosin, cathepsin B and renin.

Bovine liver catalases have normally been chosen for neutralization of hydrogen peroxide solutions for disinfection of contact lenses. However, due to fear that a slow-virus disease (Bovine Spongiform Encephalopathy (BSE)), which have been identified in European cattle herds, might spread to man, a need to find an alternative to bovine liver catalase have been sought.

The risk of spreading the slow-virus disease to man can be avoided by using microbial catalases, such as catalases derivable from bacteria, filamentous fungi or yeasts.

The stability of microbial catalases, such as e.g. the microbial catalases mentioned below, are better at acidic pHs in comparison to "standard" bovine liver catalase. Consequently it is advantageous to use microbial catalases for neutralization of hydrogen peroxide in disinfecting solutions for contact lenses with an acidic pH.

A few such suitable microbial catalases have been suggested for contact lens purposes. Catalases derived from the filamentous fungus *Aspergillus niger* have even been shown to posses properties which makes them superior to bovine liver catalases.

*Aspergillus niger* produces two catalases designated Catalase-A (CatA) and Catalase-R (CatR). CatR is four time as effective than "standard" bovine liver catalase in application requiring neutralization of a concentrated hydrogen peroxide solution. In other words CatR neutralizes hydrogen peroxide in conventional disinfecting solution (i.e. 3 wt. % $H_2O_2$, pH 3.5) much faster than standard bovine liver catalase. Further, CatR is more stable than bovine liver catalase toward proteolysis, extreme pH, temperature, hydrogen peroxide and inactivation by glutaraldehyde, SDS, etc. (see WO 93/17721 from Genencor).

Furthermore, CatR is substantially active at pH in the presence of 3 wt. % hydrogen peroxide from at least pH 3.0 and 7.0, while the activity of conventional bovine liver catalase decreases drastically from pH 7.0 toward pH 3.0.

According to the present invention it has been found that a microbial catalase being substantially active at pH 3.0 to 7.0, preferably at pH 3.0 to 4.5, may advantageously be used for neutralization of hydrogen peroxide in aqueous disinfecting solutions for contact lenses together with a protease being irreversibly inactivated within a period of time in the disinfecting solution at a pH not acceptable to the eyes. Example 1 shows that Subtilisin A is a such suitable protease.

"A catalase being substantially active" at pH 3.0 to 7.0, preferably 3.0 to 4.5, defines a catalase having a relative enzymatic activity within said pH-ranges (pH-optimum defines 100%) higher than 60%, better 70%, even better more than 80%, such as 90%, and in the best case up to about 100%.

The combination of a protease being inactivated within a period of time at a pH level not acceptable to the eyes and a microbial catalase for disinfection and cleaning of contact lenses results in a very fast one-step process and a system being very safe and consumer convenient.

Further, said combination secure that the one-step method of the invention results in a fast and efficient disinfection of the contact lenses, as the protease removes the soil matrix in which the bacteria (to be killed by the hydrogen peroxide) are present. Consequently, due to this the accessibility for the hydrogen peroxide to the bacteria is very good. As the microbial catalase is active within a broad pH range the neutralization can occur immediately reducing the period of time needed for performing the total disinfecting and cleaning task.

The microbial catalase may advantageously be any of the catalases mentioned above, such as an *Aspergillus niger* catalase, in particular CatR.

The microbial catalase may also be the *Aspergillus niger* catalase disclosed by Novo Nordisk A/S in 1990 for neutralization of hydrogen peroxide in aqueous disinfecting solutions for contact lenses.

At present it is believed that the best mode of the present invention is obtained by combining the serine protease subti-lisin A (available from Novo Nordisk as Cleanlens®Pro), as the protease, and the *A. niger* catalase named CatR described in WO 93/17721, as the microbial. In this specific embodiment the protease will be irreversibly inactivated at a pH level in the range between 1.0 to 4.5 within a suitable period of time.

The agent capable of adjusting the pH in the aqueous disinfecting solution may be any suitable agent acceptable to the eyes. For instance the pH adjusting agent may be a buffer, an acid or a base.

The purpose of the pH adjustment is to secure that the contact lenses safely can be entered directly from the aqueous disinfecting solution into the eyes, without any risk of damaging the eyes.

A suitable buffer may be selected from the group of buffers including alkali metal salts, such as potassium or sodium carbonates, acetates, borates, sodium or potassium phosphates, citrates, and hydroxides, and weak acids such as acetic and boric acids.

In the second aspect the invention relates to a tablet, capsule or the like which uses the principles of the method of the invention.

Even though it is believed that the optimal way to introduce the protease, catalase, and pH adjusting agent into the aqueous disinfecting solution is in the form of a tablet or the like, it is to be understood that also other embodiments have been contemplated by the inventors and should be regarded as encompassed by the scope of the present invention. For instance, the protease, catalase and pH adjusting agent may be added to the aqueous disinfecting solution as liquids or a combination of liquids and solids.

A multi layer tablet constructed for one-step disinfection and cleaning of contact lenses comprises (i) a protease being irreversibly inactivated within a period of time in an aqueous disinfecting solution at a pH not acceptable to the eyes, and (ii) a microbial catalase being substantially active at pH 3.0 to 7.0, (iii) an agent capable of adjusting the aqueous disinfecting solution to a pH acceptable to the eyes.

The definition of ". . . a pH level not acceptable to the eyes", and ". . . a pH level acceptable to the eyes" is described above.

The tablet may have any suitable embodiment. Four suitable embodiments will be described as examples below. The action of the four embodiments of the tablet (i.e. A, B, C and D), when used for one-step disinfection and cleaning, will also be described below.

In the first embodiment the multi-layer tablet A comprises (a) an outer layer or coating comprising said microbial catalase being substantially active at pH 3.0 to 7.0, and (b) a layer within said outer layer comprising a protease being irreversibly inactivated within a period of time in an aqueous disinfecting solution at a pH level not acceptable to the eyes, and (c) an agent capable of adjusting the disinfecting solution to a pH acceptable to the eyes.

In the second embodiment the multi layer tablet B comprises (a) an outer layer or coating comprising a protease being irreversibly inactivated within a period of time in an aqueous disinfecting solution at a pH level not acceptable to the eyes, and (b) a layer within said outer layer comprising said microbial catalase being substantially active at pH 3.0 to 7.0, and (c) an agent capable of adjusting the disinfecting solution to a pH acceptable to the eyes.

In a third embodiment the multi layer tablet C comprises (a) an outer layer or coating comprising a protease being irreversibly inactivated within a period of time in an aqueous disinfecting solution at a pH not acceptable to the eyes, (b) a layer within said outer layer comprising an agent capable of adjusting the disinfecting solution to a pH acceptable to the eyes, and (c) a core comprising a microbial catalase being substantially active at pH 3.0 to 7.0.

In the forth embodiment the multi layer tablet D comprises (a) an outer layer or coating comprising a protease being irreversibly inactivated within a period of time in an aqueous disinfecting solution at a pH not acceptable to the eyes and a microbial catalase being substantially active at pH 3.0 to 7.0, and (b) a core comprising an agent capable of adjusting the aqueous disinfecting solution to a pH acceptable to the eyes.

The protease and microbial catalase may be any of the above mention proteases and catalases.

The broad pH activity level of the microbial catalase is advantageous as adjustment to a precise pH in an aqueous disinfecting solution becomes less crucial, which again render the strict and timely control of the release of the catalase layer in the tablet less important.

Said pH adjusting agent may be any suitable agent, such as a buffer or an acid or a base which is capable of adjusting the pH in the aqueous disinfecting solution to a level acceptable to the eyes.

The core and layers of the multi tablet may be separated by a barrier or a membrane. Said barrier may in an embodiment of the invention be made of a water soluble polymer layer, preferably a water soluble film.

Examples of said water soluble film comprises polymers soluble in an acidic medium, such as polymers of dimethylaminomethacrylate and neutral methacrylate esters.

Alternatively the film comprises a pH neutral soluble polymer. Suitable polymers are e. g. soluble cellulose ethers, such as methylcellulose, methylhydroxycellulose, methylhydroxyethylcellulose, hydroxypropylcellulose, hydroxypropylmethylcellulose, hydroxyethylcellulose, sodium carboxymethylcellulose, cellulose acetate phthalate, hydroxypropylmethylcellulose phthalate, a polymer of methacrylic acid and methacrylate esters, a copolymer of methacrylic acid and methacrylate esters, a copolymer of methyl vinyl ether and maleic acid anhydride and polyvinyl alcohols.

In still another embodiment the tablet comprises a sparingly soluble core and one or two outer layers having the active constituents dispersed or distributed.

Suitable plasticizers of polyhydric alcohols and water may be added to the above listed soluble film polymers to control the diffusion rate. Preferred plasticizers for this purpose are 1,2-propylene glycol, polyethylene glycols and citrate esters.

In a preferred embodiment the tablet is a controlled release tablet of the type where the content in the outer layer is first released followed by content in the second layer after a period of time, and finalized by the release of the core content after a period of time. One of or both layers or the core content may be released slowly.

The release time of the pH adjusting agent should be so long that the protease has sufficient time to degrade composites on the contact lenses' surface.

As the catalase is substantially active within a broad pH range the neutralization ability of the catalase is not dependent on the action of the pH adjusting agent.

In a further embodiment of the invention the content in the second layer and/or core content is(are) released delayed to the aqueous disinfecting solution.

Additional components may be added to or incorporated into the tablet or capsule which do not substantially decrease the activity of the active components.

Examples are components such as effervescing agents, stabilizers, chelating agent and/or sequestering agents, colouring agent, tonicity adjusting agents, surfactant and the like. In addition binders, lubricants, carriers, and other excipients normally used in producing tablets may be incorporated.

Effervescing agents are typically employed when the enzymes are provided in solid form. Examples of suitable effervescing agent include, tartaric or citric acid used in combination with suitable alkali metal salts, such as sodium carbonate.

As the tablet of the invention is to be used in an aqueous disinfecting solution it may contain one or more of suitable chelating agents and/or sequestering agent, tonicity adjusting agent and surfactant.

Suitable tonicity adjusting agents include sodium and potassium chloride, dextrose, calcium and magnesium chloride.

Suitable surfactants can either be cationic, anionic, nonionic or amphoteric. Preferred surfactants are neutral or nonionic.

Specific examples include polyethylene glycol ethers of fatty acids, polyoxypropylene ethers of C12–C18 alkanes and polyxyethylene, polyoxypropylene block copolymers of ethylene diamine (i.e. poloxamine).

Examples of preferred chelating agents include Ethylenediaminetetraacetic acid (EDTA) and its salts (disodium) and certain polyvinyl alcohols.

The tablet of the invention constitutes together with an aqueous disinfecting solution comprising 1 wt. % to 5 wt. % hydrogen peroxide a one-step disinfecting and cleaning system for contact lenses.

An ideal consumer convenient disinfection and cleaning procedure is carried out in only one continuous step, e.g. in connection with storing the contact lenses for the night, resulting in that the contact lenses are ready for wearing directly from the storage container the next morning without any additional work.

According to the invention the contact lens user only need to introduce the contact lenses into a fix amount of an aqueous disinfecting solution comprising hydrogen peroxide and add a tablet the invention. Said tablet perform the cleaning and disinfection task and further neutralizes the hydrogen peroxide in a safe manner.

Consequently, the one-step system of the invention reduces the work to be done for the contact lens user when performing the disinfecting and cleaning task; facilitates the disinfecting and cleaning task, as only one continuous step need to be performed; eliminates the risk of using the system incorrectly, (e.g. forgetting to neutralize the contact lenses after disinfection and/or cleaning before wear), as the procedure can be performed continuously within few seconds.

The one-step system of the invention comprises
(a) an aqueous disinfecting solution comprising 1 wt. % to 5 wt. % hydrogen peroxide, and
(b) a tablet or capsule comprising
  (i) a protease being irreversibly inactivated within a period of time in an aqueous aqueous disinfecting solution at a pH not acceptable to the eyes, and
  (ii) a microbial catalase being substantially active at pH 3.0 to 7.0 for neutralizing the hydrogen peroxide, and
  (iii) an agent capable of adjusting the pH in the aqueous disinfecting solution to a pH level acceptable to the eyes.

In a preferred embodiment of the invention hydrogen peroxide is present in the aqueous disinfecting solution in 3 wt. % (pH 3.5).

The tablet or capsule of the invention may advantageously be used as a constituent in the one-step system of the invention.

In the following one-step disinfecting and cleaning of contact lenses using tablet A, B, C and D is roughly described.

One-step Disinfection and Cleaning Using Tablet A

The contact lenses are immersed in a conventional 3 wt. % hydrogen peroxide disinfecting solution (pH 3.5) together with multi layer tablet A. Initially the hydrogen peroxide disinfects the contact lenses. The microbial catalase (comprised in the outer layer) is released leading to neutralization of the hydrogen peroxide in the aqueous disinfecting solution. After a period of time the protease (comprised in the layer below the outer layer) is released into the disinfecting solution and the contact lenses are cleaned. Within a period of time the protease is irreversibly inactivated. Finally the buffer (comprised in the core of the tablet) is released resulting in that the pH increases to a pH acceptable to the eyes. The contact lenses are ready to wear directly from the aqueous disinfecting solution.

One-step Disinfection and Cleaning Using Tablet B

The contact lenses are immersed in a conventional 3 wt. % hydrogen peroxide disinfecting solution (pH 3.5) together with multi layer tablet B. Initially the hydrogen peroxide disinfects the contact lenses. The protease (comprised in the outer layer) is released into the disinfecting solution and cleans the contact lenses. Within a period of time the protease is irreversibly inactivated. After a period of time the microbial catalase (comprised in the layer below the outer layer) is released resulting in neutralization of the hydrogen peroxide in the disinfecting solution. Finally the buffer (comprised in the core of the tablet) is released increasing the pH to a level acceptable to the eyes. The lenses are ready to wear directly from the aqueous disinfecting solution.

One-step Disinfection and Cleaning Using Tablet C

The contact lenses are immersed in a conventional 3 wt. % hydrogen peroxide disinfecting solution (pH 3.5) together with multi layer tablet C. Initially the hydrogen peroxide disinfects the contact lenses. The protease (comprised in the outer layer) is released into the disinfecting solution and cleans the contact lenses. Within a period of time the protease is irreversibly inactivated. After a period of time the buffer (comprised in the layer below the outer layer) is released resulting in that the pH is increased to a level acceptable to the eyes. The catalase (comprised in the core of the tablet) is released resulting in neutralization of the hydrogen peroxide in the aqueous disinfecting solution. The lenses are ready to wear directly from the aqueous disinfecting solution.

One-step Disinfection and Cleaning Using Tablet D

The contact lenses are immersed in a conventional 3 wt. % hydrogen peroxide disinfecting solution (pH 3.5) together with multi layer tablet D. Initially the hydrogen peroxide disinfects the contact lenses. The protease and the microbial catalase (comprised in the outer layer) are released into the disinfecting solution. The contact lenses are cleaned by the protease and the hydrogen peroxide is neutralized by the catalase. Within a period of time the protease is irreversibly inactivated. After a period of time the buffer (comprised in the core of the tablet) is released resulting in that the pH is increased to a level acceptable to the eyes. The lenses are ready to wear directly from the aqueous disinfecting solution.

The above examples of one-step disinfection and cleaning proves the advantageous use of the combination of a protease and a microbial catalase.

As the microbial catalase (in contrast to bovine liver catalase) is active at pH 3.5 the catalase can neutralize the hydrogen peroxide at the same time as the protease cleans the contact lenses.

Finally the invention relates to a one-step procedure for disinfecting and cleaning contact lenses, comprising the steps of
(1) soaking the contact lenses in a fixed amount of an aqueous disinfecting solution comprising 1 wt. % to 5 wt. % hydrogen peroxide, preferably 3 wt. %, (2) adding a tablet according to the invention, and (3) storing the contact lenses in the aqueous disinfecting solution for a period of time.

The aqueous disinfecting solution must constitute a fixed amount which will normally be between 1 ml and 10 ml, especially about 5 ml.

The storage period needed in step 3) depend of the formulation. In general the tablet is formulated so that the contact lenses must be stored for between 10 minutes and 12 hours, preferably between 15 minutes and 4 hours, especially between 20 minutes and 2 hours.

Materials and Methods

Subtilisin A (available from Novo Nordisk as Cleanlens®Pro),

Proteolytic Activity

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e. 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novo Nordisk A/S, Denmark, which folder is hereby included by reference.

EXAMPLES

Example 1

Stability of Subtilisin A with/without 3 wt. % hydrogen peroxide

The pH-stability of Subtilisin A (available from Novo Nordisk as Cleanlens®Pro), was determined by letting an enzyme solution (0.0003 AU/ml) stand for between 0 to 240 minutes, at 25° C. and different pH-values (from pH 2 to 7) and measure proteolytic activity before and after standing.

The result of the test shown as relative enzymatic activity is displayed in Table 1 and Table 2 below. For each pH, the zero-time activities have been set to 100%.

TABLE 1 pH stability of Subtilisin A without the presence of $H_2O_2$

| Minutes | pH 2 | pH 3 | pH 4 | pH 5 | pH 7 |
|---|---|---|---|---|---|
| 0 | 100 | 100 | 100 | 100 | 100 |
| 15 | 0 | 21 | 79 | n.d | n.d |
| 30 | 0 | 22 | 49 | n.d | n.d |
| 60 | 0 | 8 | 14 | 88 | 95 |
| 120 | n.d. | n.d. | n.d. | 77 | 94 |
| 240 | n.d. | n.d. | n.d. | 67 | 106 | n.d: not determined

TABLE 2 pH stability of Subtilisin A in the presence of 3% $H_2O_2$

| Minutes | pH 3 | pH 4 | pH 5 | pH 7 |
|---|---|---|---|---|
| 0 | 100 | 100 | 100 | 100 |
| 15 | 0 | 6 | 18 | 13 |
| 30 | 0 | 0 | 5 | 13 |
| 60 | 0 | 0 | 0 | 15 |
| 120 | n.d. | n.d. | 0 | 14 |
| 240 | n.d. | n.d. | n.d. | 12 | n.d.: not determined

As can be seen from Table 1 Subtilisin A is stable at pH 7 in the absence of $H_2O_2$. Table 2 shows that Subtilisin A is very unstable at pHs from below 7.

What is claimed:

1. A method for disinfecting and cleaning contact lenses comprising the steps of
   (a) disinfecting the contact lenses in an aqueous disinfecting solution comprising from 1 wt. % to 5 wt. % hydrogen peroxide at a pH not acceptable to the eyes,
   (b) cleaning the contact lenses by subjecting the contact lenses to an alkalophilic subtilisin protease, said protease being inactivated within a period of time by a pH between about 1.0 and about 6.0,
   (c) neutralizing the hydrogen peroxide in the aqueous disinfecting solution with a microbial catalase said catalase being substantially active at pH 3.0 to 7.0, and
   (d) adjusting the pH in the aqueous disinfecting solution to a pH level acceptable to the eyes.

2. The method of claim 1, following the step sequence a)-b)-c)-d).

3. The method of claim 2, wherein steps (b) and (c) are performed simultaneously.

4. The method of claim 1, following the step sequence a)-c)-b)-d).

5. The method of claim 1, following the step sequence a)-b)-d)-c).

6. The method of claim 1, wherein the aqueous disinfecting solution comprises about 3 wt. % hydrogen peroxide at about pH 3.0 to 4.5.

7. The method of claim 1, wherein the alkalophilic subtilisin is subtilisin A.

8. The method of claim 1, wherein the protease is inactivated at a pH between about 1.0 and about 4.5.

9. The method of claim 1, wherein the microbial catalase is derivable from a bacteria, a filamentous fungus or a yeast.

10. The method of claim 9, wherein the microbial catalase is derivable from Aspergillus sp.

11. The method of claim 10, wherein the microbial catalase is derivable from *Aspergillus niger*.

12. The method of claim 11, wherein the catalase is CatA or CatR.

13. A tablet for disinfecting and cleaning contact lenses, comprising
   (i) an alkalophilic subtilisin protease, said protease being irreversibly inactivated within a period of time in an aqueous disinfecting solution at a pH between about 1.0 and 6.0,
   (ii) a microbial catalase, said catalase being substantially active at pH 3.0 to 7.0,
   (iii) an agent capable of adjusting the disinfecting solution to a pH acceptable to the eyes.

14. The tablet of claim 13, comprising
   (a) an outer layer or coating comprising said microbial catalase, (b) a layer within said outer layer comprising said protease, and (c) a core comprising said pH adjusting agent.

15. The tablet of claim 13, comprising (a) an outer layer or coating comprising said protease, (b) a layer within said outer layer comprising said microbial catalase, and (c) a core comprising said pH adjusting agent.

16. The tablet of claim 13, comprising (a) an outer layer or coating comprising said protease and said microbial catalase, and (b) a core comprising said pH adjusting agent.

17. The tablet of claim 13, wherein the catalase is derivable from a bacteria, a filamentous fungus or a yeast.

18. The tablet of claim 13, wherein said tablet is a controlled release tablet.

19. The tablet of claim 13, being of the controlled release type, wherein the content of the outer layer is released first, and said content of the second layer is released secondly after a period of time, and the core content is released last after a period of time.

20. A disinfecting and cleaning system for contact lenses comprising (a) an aqueous disinfecting solution comprising 1 wt. % to 5 wt. % hydrogen peroxide, and (b) a tablet comprising (i) an alkalophilic subtilisin protease, said protease being irreversibly inactivated within a period of time in an aqueous disinfecting solution at a pH between about 1.0 and 6.0, and (ii) a microbial catalase, said catalase being substantially active at pH 3.0 to 7.0, (iii) an agent capable of adjusting the aqueous disinfecting solution to a pH acceptable to the eyes.

21. The system of claim 20, wherein the hydrogen peroxide in the aqueous disinfecting solution is present in a concentration between 1 wt. % to 5 wt. % at a pH in the range between 3.0 to 4.5.

22. The system of claim 20, wherein the pH adjusting agent is a buffer, or a base.

23. The system of claim 22, wherein the pH adjusting agent is a buffer capable of adjusting the pH in the aqueous disinfecting solution to a pH where the enzyme is irreversibly inactivated.

24. The system of claim 23, wherein the buffer adjusts the pH in the aqueous disinfecting solution to a pH acceptable to the eyes.

25. A procedure for disinfecting and cleaning contact lenses, comprising the steps of (1) soaking the contact lenses in a fixed amount of an aqueous disinfecting solution comprising 1% to 5% hydrogen peroxide, and (2) adding a tablet comprising (i) an alkalophilic subtilisin protease, said protease being irreversibly inactivated within a period of time in an aqueous disinfecting solution at a pH between about 1.0 and about 6.0.

(ii) a microbial catalase, said catalase being substantially active at pH 3.0 to 7.0.

(iii) an agent capable of adjusting the disinfecting solution to a pH acceptable to the eyes, and (3) storing the contact lenses in the disinfecting solution for a period of time.

26. The procedure of claim 25, wherein the aqueous disinfecting solution comprises about 3% hydrogen peroxide at a pH in the range of 3.0 to 4.5.

27. The procedure of claim 25, wherein the fixed amount of aqueous disinfecting solution comprising hydrogen peroxide is from 1 ml to 10 ml.

28. The procedure of claim 25, wherein the contact lenses is stored in the aqueous disinfecting solution for between 5 minutes and 12 hours.

* * * * *